(12) United States Patent
Muzzammel

(10) Patent No.: US 7,033,355 B2
(45) Date of Patent: Apr. 25, 2006

(54) ENDOCERVICAL ELECTRODE

(76) Inventor: Mohiuddin M. Muzzammel, 11323 Bright Pond La., Reston, VA (US) 20194

( * ) Notice: Subject to any disclaimer, the term of this patent is extended or adjusted under 35 U.S.C. 154(b) by 156 days.

(21) Appl. No.: 10/757,481

(22) Filed: Jan. 15, 2004

(65) Prior Publication Data

US 2005/0159744 A1    Jul. 21, 2005

(51) Int. Cl.
*A61B 18/14* (2006.01)
(52) U.S. Cl. .................................... 606/45; 600/564
(58) Field of Classification Search ................ 606/45, 606/564
See application file for complete search history.

(56) References Cited

U.S. PATENT DOCUMENTS

| 712,989 | A | * | 11/1902 | Washburn | 606/29 |
|---|---|---|---|---|---|
| 1,794,296 | A | * | 2/1931 | Hyams | 606/45 |
| 5,032,124 | A | | 7/1991 | Menton | 606/19 |
| 5,403,310 | A | * | 4/1995 | Fischer | 606/45 |
| 5,505,728 | A | | 4/1996 | Ellman et al. | 606/39 |
| 5,527,331 | A | | 6/1996 | Kresch et al. | 606/170 |
| 5,554,159 | A | | 9/1996 | Fischer | 606/45 |
| 5,676,663 | A | | 10/1997 | Kim | 606/45 |
| 5,683,387 | A | | 11/1997 | Garitoe | 606/45 |
| 5,951,550 | A | | 9/1999 | Shirley et al. | 606/45 |
| 6,068,628 | A | | 5/2000 | Fanton et al. | 606/41 |
| 6,267,759 | B1 | | 7/2001 | Quick | 606/47 |
| 6,416,513 | B1 | | 7/2002 | Dresden | 606/45 |
| 6,575,970 | B1 | * | 6/2003 | Quick | 606/45 |

* cited by examiner

*Primary Examiner*—Lee S. Cohen
(74) *Attorney, Agent, or Firm*—Patent & Trademark Services, Inc.; Joseph H. McGlynn

(57) ABSTRACT

An electrode for the excision of a circular segment of an entire cervical canal. The electrode has a parallel wire, at one end, which can be rotated 360 degrees. This enables a single instrument to remove an entire cervical canal, instead of using different sized instruments.

4 Claims, 1 Drawing Sheet

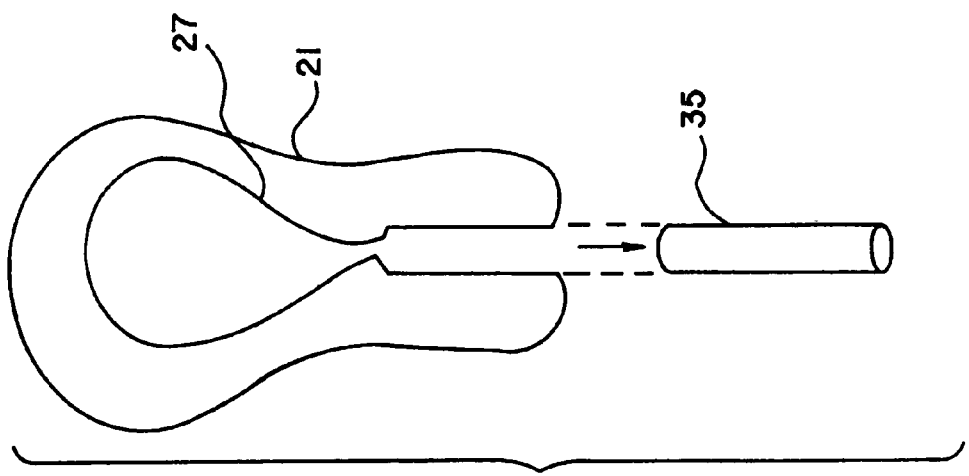
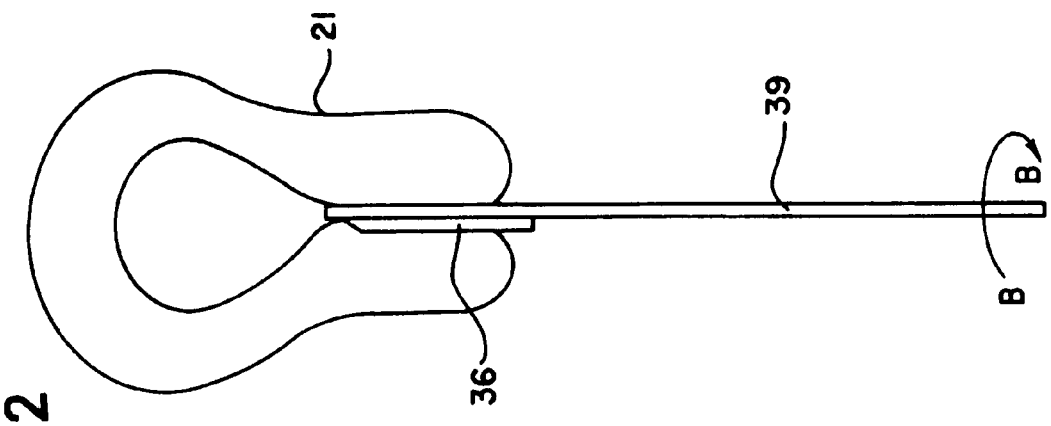
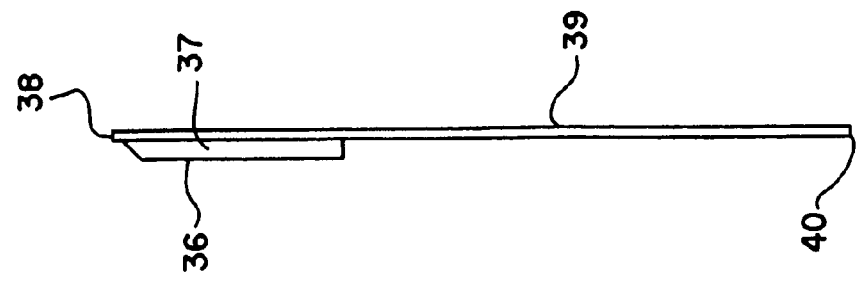

ENDOCERVICAL ELECTRODE

BACKGROUND OF THE INVENTION

This invention relates in general to an electrode and in particular to an electrode used for excision of the entire cervical canal.

Using electrodes to remove tissue from a human or other animal are known. A laser beam may be used in this process. When using such a beam, a guiding tubular structure can be employed to direct the beam to the desired location where it may be deflected by a deflection member. This action can allow the laser beam to sweep in a conical configuration. Another electro-surgical instrument used for excision of a tissue finds particular use in the transformation zone of the uterine cervix. In that particular instrument a stop arm is used.

Still another type of related instrument is referred to as a cone biopsy instrument and has a cuff of electrical insulating material, a core positioned within the cuff having an electrical conductor, a wire carrier of electrical insulating material with projecting arms, an electrically conducting wire connected between a wire carrier arm and the core, an implant sleeve freely rotating on the swaged portion of the core between the wire carrier and tip, and a cervical guide tip of electrical insulating material carried on the core. Another type of instrument is entitled an endocervical conization electrode apparatus. This instrument is used for excising a tissue specimen from a uterine cervix having a substantially constant section. In that instrument an electrode is used for excising tissue and has an extension member.

Still another common type of electrode currently being used to remote tissue is the loop electrode excision procedure (LEEP). With the LEEP, loops of various shapes and sizes, at least nine, are used. These loops may be different sizes and semicircular in shape with different radiuses, or the loops may be rectangular in shape and different sizes. Specific sizes and shapes are employed depending on the depth of the tissue to be removed and the width of the removed tissue. The size and location of the tissue to be removed and the size of the patient's cervix are also factors considered in selecting the particular loop used in the LEEP.

In the present invention, one instrument is used to replace the many different sizes and shapes of cone biopsy electrodes for excision of tissue with various widths and depths of abnormalities, in the cervical canal. The electrode of the present invention removes the entire cervical canal, compared to a cone biopsy electrode which removes only part of the cervical canal. The electrode of the present invention also prevents lateral injury to the cervix, which is common with cone biopsy electrodes.

DESCRIPTION OF THE PRIOR ART

Using electrodes for excising tissue from a human or other animal is known in the prior art. For example, U.S. Pat. No. 5,032,124 to Menton discloses an electrode for excising tissue which has a hollow tube through which a laser beam can be passed.

U.S. Pat. No. 5,554,159 to Fischer discloses an electrode for excising tissue which has a stop arm which is positioned at a right angle to the electrode.

U.S. Pat. No. 5,676,663 to Kim discloses an electrode for excising tissue which has a plurality of radially projecting arms.

U.S. Pat. No. 5,951,550 to Shirley et al. discloses an electrode for excising tissue which has an extension member extending radially from the electrode.

The present invention is directed to an electrode for excision of tissue from the cervix and which can be rotated 360 degrees at one end, all as will be detailed in the specification that follows hereafter.

SUMMARY OF THE INVENTION

This invention relates to an electrode for the excision of tissue from the cervix. The electrode has a fine wire, at one end, which can be rotated 360 degrees thereby removing an entire lesion. This enables a single instrument to remove lesions, instead of using different sized instruments.

It is the primary object of the present invention to provide for an improved electrode for the excision of tissue.

Another object is to provide for such an electrode that is designed for use in the cervix and which allows different sized cervixes and different sized lesions to be treated with the same instrument.

These and other objects and advantages of the present invention will become apparent to readers from a consideration of the ensuing description and the accompanying drawings.

BRIEF DESCRIPTION OF THE DRAWINGS

FIG. 1 is a side view of the present invention.

FIG. 2 is a side view of the present invention in position inside the cervix.

FIG. 3 is a view of the lesion removed from the cervix.

FIG. 4 is a partial view of the electrode of the present invention.

DESCRIPTION OF THE PREFERRED EMBODIMENT

FIG. 1 shows a side view of the present invention. The electrode has a handle 39 with a first end 38 and a second end 40. A conducting wire 36 is attached to the handle 39 in any conventional manner. A means of conducting electricity to the wire 36 through the handle 39 will be provided, however, since this type of electricity providing device is conventional it is not shown in FIG. 1 for purposes of clarity. The wire 36 is attached closer to the end 38 than to the end 40 so the user has enough room to grasp the handle and to manipulate the device. The wire 36 has two ends which are attached so a space 37 extends between the wire 36 and a surface of the handle 39. the end of the wire closest to end 38 has an attachment means which is sloped to facilitate easy insertion into the cervical canal 27. The opposite end does not have to be sloped since it will not, under normal conditions, enter the canal (see FIG. 2).

FIG. 2 shows the electrode in position inside the cervix 21. In order to use the electrode the operator rotates the handle as shown by the arrows BB in a complete 360∞ circle. By rotating in a complete circle, the entire lesion can be removed in a single procedure. Also, by manipulating the device in a horizontal direction the operator can remove different size lesions with only one instrument. That is, different sized instruments will not have to be used for different sized lesions.

As shown in FIG. 3 the use of the present invention on the cervical canal 27 will remove a circular plug shape 35. The removal will occur in one simple procedure, and will be performed with a single instrument.

FIG. 4 shows a partial view of the end of the device of the present invention. As shown in FIG. 4 the support for the wire or electrode 36 is triangular in cross-section in order to provide a strong support for the electrode. The triangular shape will help prevent unwanted deflection of the electrode 36. Also, as shown in FIGS. 1 and 4, the wire or electrode 36 is held parallel to the surface of the handle 39 which faces the electrode (or to the longitudinal axis of the handle). This position will be held due to the triangular shape of the electrode support. The parallel position of the electrode will produce the circular excision as shown at 35 in FIG. 3.

Although the preferred embodiment of the present invention and the method of using the same has been described in the foregoing specification with considerable details, it is to be understood that modifications may be made to the invention which do not exceed the scope of the appended claims and modified forms of the present invention done by others skilled in the art to which the invention pertains will be considered infringements of this invention when those modified forms fall within the claimed scope of this invention.

The invention claimed is:

1. An electrode for the excision of tissue comprising:
a handle having a length and a width,
   said handle having a first end and a second end, and
   an electrically conducting wire attached to said handle,
   said electrically conducting wire being attached closer to said first end of said handle than to said second end of said handle, and
   said electrically conducting wire being disposed parallel to a longitudinal axis of said handle, and
wherein said electrically conducting wire has a support,
   said support secures said electrically conducting wire to said handle, and
   said support is triangular in cross-section.

2. The electrode as claimed in claim 1, wherein said support has a first end and a second end, and
   said first end of said support is closer to said first end of said handle than to said second end of said handle, and
   said first end of said support is slanted.

3. The electrode as claimed in claim 1, wherein said support has a first end and a second end, and
   said first end of said support is closer to said first end of said handle than to said second end of said handle, and
   said first end of said support makes an acute angle with said longitudinal axis of said handle.

4. The electrode as claimed in claim 1, wherein said elecirode has a parallel electrode wire which can be placed in the cervical canal and can be rotated 360 degrees, and
   said electrode wire will remove a circular segment of an entire cervical canal.

* * * * *